(12) United States Patent
Tiarks et al.

(10) Patent No.: US 6,562,296 B1
(45) Date of Patent: May 13, 2003

(54) PROCESS FOR CLEANING SURGICAL INSTRUMENTS

(75) Inventors: Petra Tiarks, Hamburg (DE); Jürgen Staffeldt, Winsen/Luhe (DE)

(73) Assignee: Chemische Fabrik Dr. Weigert GmbH & Co. KG, Hamburg (DE)

( * ) Notice: Subject to any disclaimer, the term of this patent is extended or adjusted under 35 U.S.C. 154(b) by 0 days.

(21) Appl. No.: 09/529,045

(22) PCT Filed: Oct. 8, 1998

(86) PCT No.: PCT/EP98/06396

§ 371 (c)(1),
(2), (4) Date: Apr. 5, 2000

(87) PCT Pub. No.: WO99/18184

PCT Pub. Date: Apr. 15, 1999

(30) Foreign Application Priority Data

Oct. 8, 1997 (DE) .......................................... 197 44 434

(51) Int. Cl.[7] ................................................. A61L 2/00
(52) U.S. Cl. ................................. 422/28; 134/2; 134/3; 134/39; 134/41; 134/42; 422/1; 422/34; 510/203; 510/206; 510/210
(58) Field of Search ................................. 422/28, 34, 1; 134/3, 2, 39, 41, 42; 510/175–176, 203, 206, 210

(56) References Cited

U.S. PATENT DOCUMENTS

| 4,077,898 | A | * | 3/1978 | Rue ............................... 134/2 |
| 4,243,546 | A | | 1/1981 | Shaer |
| 5,810,944 | A | * | 9/1998 | Smitkowski et al. ......... 134/42 |
| 6,372,050 | B2 | * | 4/2002 | Honda et al. .................. 134/2 |

FOREIGN PATENT DOCUMENTS

| EP | 0 481663 B1 | 1/1996 |
| EP | 0 730 024 A1 | 9/1996 |
| GB | 2 053 954 A | 2/1981 |
| GB | 2 068 405 A | 8/1981 |
| GB | 2 204 321 A | 11/1988 |
| WO | WO 94/02179 | 2/1994 |

* cited by examiner

Primary Examiner—Krisanne Thornton
(74) Attorney, Agent, or Firm—Medlen & Carroll, LLP.

(57) ABSTRACT

The present invention relates to the use of a cleaning composition concentrate in particular for the mechanical cleaning of medical and/or surgical instruments and/or apparatuses and to a process for carrying out this cleaning.

52 Claims, No Drawings

PROCESS FOR CLEANING SURGICAL INSTRUMENTS

The present invention relates to the use of a cleaning composition concentrate in particular for the mechanical cleaning of medical and/or surgical instruments and/or apparatuses and to a process for carrying out this cleaning.

Surgical instruments and other medical equipment are conventionally mechanically cleaned in the hospital using alkaline cleaning compositions and are then chemically or thermally disinfected. Such strongly alkaline media can act aggressively towards sensitive surfaces. Blood-contaminated surgical instruments are frequently deposited immediately after their use, for example, into an aldehyde-containing disinfectant solution and initially remain therein until they are cleared out into the dishwasher for cleaning. The blood is coagulated by the disinfectants and the protein constituents present in the blood are denatured by the aldehyde active disinfectant compound. Particularly persistent blood residues of this type may frequently only be removed by alkaline active-chlorine-containing cleaning compositions. The oxidizing active chlorine component causes the decomposition of the denatured protein constituents. Other constituents of disinfectants, for example iodine, can also form residues which are difficult to remove.

The alkaline active-chlorine-containing cleansers have the disadvantages that they comprise dangerous substances which are subject to declaration, that special safety precautions are necessary during their handling to protect the operating personnel and that they constitute an unwanted environmental pollution in the wastewater.

U.S. Pat. No 4,243,546, EP-A-0 481 663 and EP-A-0 730 024 disclose enzyme-containing cleaning compositions which can enzymatically degrade in particular blood proteins. It is proposed there to use triethanolamine for stabilizing the enzymes. Disadvantages of these cleansers are the high price of the enzymes, their heat sensitivity and the decay of the enzyme activity during relatively long storage, in particular at relatively high temperatures.

The object underlying the invention is to provide a process for cleaning medical and/or surgical instruments and/or apparatuses in which the disadvantages of the active-chlorine-containing and enzymatic cleansers do not occur or occur to a relatively small extent and which nevertheless ensures a sufficient cleaning action.

The invention achieves this object by the features of claims 1 and 13. Advantageous developments are specified in the subclaims.

The invention thus relates to the use of an enzyme-free cleaning composition concentrate which comprises at least 10% by weight of at least one alkanolamine for cleaning medical and/or surgical instruments and/or apparatuses.

Although alkanolamine-containing enzymatic cleansers are already known in the prior art, only an enzyme-stabilizing action is ascribed there to the alkanolamine (U.S. Pat. No. 4,243,546), and the actual cleaning agent is said to be the enzymatic active compound. Surprisingly, it has now been found, however, that an alkanolamine, as main active component of a cleaning composition, is suitable for complete removal from surgical instruments of blood residues which have dried on, been preheated or denatured by, for example, aldehyde active disinfectant compounds in the context of mechanical cleaning. The iodine residues and their reaction products with blood constituents which frequently originate from disinfectants are also removed. This cleaning action is obtained despite the omission of enzymes which are considered to be essential in the prior art.

Preferably, the alkanolamines used have the following structure:

where $R_1$ is a hydroxyalkyl group having 1 to 6 carbon atoms and $R_2$ and $R_3$ independently of one another are the said hydroxyalkyl group or hydrogen.

Particular preference is given to mono-, di- and/or tri-ethanolamine.

The alkanolamines used according to the invention are bases. It is possible in the context of the invention to use the cleanser concentrate in aqueous solution in a pH range which is established by the presence of these bases and is generally above 9, preferably above 9.5. A pH of 10.5 to 11 is generally not exceeded. An alkaline cleanser of this type can require particular safety measures during handling. Sensitive surfaces (for example anodized aluminium surfaces) can under some circumstances be attacked by a more strongly alkaline cleanser. However, the aggressivity of the cleanser made alkaline according to the invention towards anodized aluminium surfaces is markedly decreased if this cleanser does not comprise a complexing agent such as NTA. Setting the pH alkaline is advantageous for complete removal of blood/iodine residues. This good cleaning action is achieved even in the absence of complexing agents such as NTA.

In a further embodiment of the invention the cleanser concentrate in ready-to-use dilute aqueous solution has a pH of 6 to 10, preferably 7 to 9. It has proved that surprisingly the alkanolamines which are alkaline per se develop a sufficient cleaning action even in this slightly acidic to slightly alkaline region. A ready-to-use dilution is taken to mean according to the invention a 0.5–100% strength aqueous solution of the cleaning composition concentrate. When in the context of the present application pHs of a dilute solution of the cleaning composition concentrate are measured, the solvent used is demineralized water. If the concentrate is made up with standard tap water to give a ready-to-use solution, slightly differing pHs can result depending on the properties of this water.

The pH is set to the said range preferably by addition of acids and/or suitable buffer systems. Preference is given to the addition of at least one organic acid selected from the group consisting of mono-, di- or tricarboxylic acids having 2 to 6 carbon atoms. Acids which are preferred among these are citric acid, tartaric acid, malic acid, lactic acid, glycolic acid, glyoxylic acid, succinic acid, adipic acid and glutaric acid. Citric acid is particularly preferred. The acids are added to the concentrate preferably in an amount of 0.5 to 15% by weight, more preferably 2 to 10% by weight.

According to the invention, the concentrate can comprise at least one complexing agent, in particular chelating agent. The complexing agents serve for water softening and, by complexing alkaline earth metal ions, can improve the cleaning action compared with lime soaps. The complexing agents can be homo-, co- or terpolymers based on acrylic acid or alkali metal salts thereof, in addition phosphonic acids or alkali metal salts thereof, such as, for example, 1-hydroxyethane-1,1-diphos-phonic acid, aminotrismethyl-enephosphonic acid, ethylenediaminotetrakismeth-ylenephosphonic acid, phosphonobutanetricarboxylic acid; tartaric acid, citric acid and gluconic acid; and in addition nitrilotriacetic acid or ethylenediaminetetraacetic acid or salts thereof.

The concentrate of the invention can comprise nitrilotriacetic acid and/or a salt of this acid, particularly preferably its trisodium salt. This NTA addition surprisingly causes particularly good lime soap removal even at low pHs in the range 6 to 9. The NTA addition is additionally advantageous if the concentrate is to be made up to give a ready-to-use solution using (hard) water having a high mineral content.

If, owing to the necessity of using the cleanser with relatively hard water, the addition of complexing agents, such as, for example, NTA, is necessary, under some circumstances anodized aluminium surfaces can be attacked by the cleanser solution. Surprisingly, it has been found that the corrosive action of such complexing agents is decreased or avoided completely by the addition of at least one mono- and/or diester of phosphoric acid with aliphatic alcohols of chain length $C_1$ to $C_{22}$ and/or aliphatic diols and/or aliphatic polyols of chain length $C_2$ to $C_{22}$. Particular preference is given to a diester of phosphoric acid with butanol on the one hand and ethylene glycol on the other hand. This ester is commercially available under the name Hordaphos® MDGB. According to the invention, a good cleaning action is thus obtained even when hard water is used and despite a mild effect on anodized aluminium surfaces. The pH of this cleanser in which complexing agent and the said phosphoric esters are present is preferably between 9 and 11, more preferably between 9.5 and 10.5.

Customary preservatives can be added to the concentrate, for example p-hydroxybenzoic acid or its methyl ester, 5-bromo-5-nitro-1,3-dioxane, salicylic acid, 2-naphthyl m-N-dimethylthiocarbanilate, 5-chloro-5-methyl-4-isothiazolin-3-one, 2-methyl-4-isothiazolin-3-one and mixtures of the two last-mentioned compounds. A preferred preservative is p-hydroxybenzoic acid or its methyl ester. Microbial and fungal infection of cleaning composition concentrate may be avoided using these preservatives.

If necessary, formulation aids (solubilizers) can be added, such as, for example, sodium cumenesulphonate, sodium toluenesulphonate, sodium xylenesulphonate, urea, glycols, in particular polypropylene glycols and polyethylene glycols, methylacetamide and fatty alcohols, for example cetyl alcohol.

The listing of possible constituents is not final. In addition, for example wetting agents, emulsifiers, antifoaming agents or the like can be added. It is advantageous to add, for example, N-acylglutamate as wetting agent.

The alkanolamine content of the concentrate of the invention is preferably 10 to 40% by weight, more preferably 10 to 20% by weight.

Preference is given according to the invention in particular to the use of the concentrate for the cleaning carried out mechanically in dishwashers.

The invention also relates to a process for cleaning medical and/or surgical instruments and/or apparatuses having the following steps:
a) applying a 0.5–100% strength aqueous solution of an enzyme-free cleaning composition concentrate which comprises at least 10% by weight of at least one alkanolamine,
b) allowing the solution to act at a temperature from room temperature to boiling temperature of the solution,
c) rinsing [sic]

The aqueous solution of the cleaning composition concentrate is preferably applied by spraying, but it could also be applied by dipping or pouring, for example. The concentrate can be sprayed on in a very high concentration, if appropriate undiluted, as a fine mist and can initially act at this high concentration or in undiluted form. Then, if appropriate, additional water can be applied to the instruments to be cleaned and the cleaning solution thus diluted is circulated and, for example, applied again by spraying onto the instruments to be cleaned.

The action defined in step b) can include, after the application of the cleaning solution, action in the static state, i.e. without continuous application or spraying or mechanical circulation or agitation of the cleaning solution. Thus, for example, in particular highly concentrated cleaning solution can initially be sprayed on and, after the spraying, it is then allowed to act. However, the period of action can also include sections in which the cleaning solution is continuously reapplied or resprayed onto the instruments and/or is continuously mechanically circulated or agitated in some other manner. A combination of these two methods of action is also advantageous, that is initially allowing in particular highly concentrated cleanser solution to act in the static state and subsequent dilution of the cleanser with water with continuous circulation and repeated spraying.

The aqueous solution of the cleaning composition concentrate is advantageously applied as a 0.5 to 20% strength, preferably as a 0.5 to 10% strength, more preferably as a 1 to 5% strength, aqueous solution. During the period of action, the solution of the concentrate can be further diluted by additional water, but the concentration should not fall below a minimum of 0.5%. It should be noted that all percentages are by weight.

The solution is allowed to act in step b) preferably at room temperature up to 55° C., more preferably at 35–50° C., particularly preferably at 40–50° C. Temperatures of action of somewhat above 40° C. have proved to be particularly advantageous, since firstly good cleaning action is achieved and secondly the instruments to be cleaned are treated gently.

Advantageously, the time of action in step b) is 2 s to 30 min, preferably 10 s to 10 min, more preferably 30 s to 5 min.

The listing of the process steps present in claim 12 is not final. Additional prerinsing or post-rinsing steps can be provided, and a plurality of cleaning steps can also be provided one after the other. Preference is further given to an additional disinfection step which can be carried out, for example, by chemical disinfectants. Particular preference is given to carrying out a thermal disinfection. This can be carried out as a downstream step, for example using demineralized water, at 85° C. to 95° C., preferably 93° C. This water can at the same time be used for post-rinsing in accordance with step c), so that in this manner post-rinsing and thermal disinfection are combined with one another. However, the thermal disinfection step can alternatively be performed with the cleaning solution of step b) heated to the appropriate temperature instead of with fresh water.

According to the invention, the cleaning composition concentrate can be used highly successfully in the context of what is termed an RKI (BGA) programme. In this programme which is recognized by the Robert Roch Institute (RKI; formerly the German Federal Health Office (BGA)) for cleaning and simultaneous thermal disinfection of both the articles to be cleaned and the cleaning solution, the concentrate, in a one-tank dishwasher, is metered into cold incoming water. The cold cleanser solution is then (preferably with simultaneous circulation) continuously heated to 93° C. The heat-up time is primarily dependant on the heating power of the machine and is preferably between about 3 and 15 minutes. Then there is preferably an about 10-minute action at 93° C. to carry out the thermal disinfection. The hot cleanser solution can be discharged immediately into the sewage system, it requires no subsequent disinfection treatment. This cleaning step is preferably followed by intermediate rinsing and/or post-rinsing steps preferably using clean water, if appropriate also with the addition of a rinse aid.

If appropriate, when so-called discontinuous conveyor dishwashers are used, a plurality of cleaning steps can also be carried out one after the other using the cleaning composition concentrate of the invention. In this case, it is possible, for example, to use in one cleaning step an ultrasonic bath which is filled with an aqueous solution of the cleaning composition concentrate of the invention.

The invention achieves a good cleaning action, in particular even in barely accessible regions of surgical instruments, for example in the joint area of scissors.

The invention is described below with reference to exemplary embodiments.

Cleaning composition concentrates of the invention are prepared on the basis of the details in the table below. The amounts of the starting materials to be used are given in parts by weight.

|  | Example 1 | Example 2 | Example 3 | Example 4 |
|---|---|---|---|---|
| Triethanolamine 85% | 15.0 | 15.0 | 15.0 | 15.0 |
| Hordaphos ® MDGB[1)] | — | — | — | 1.0 |
| Citric acid | 8.0 | 4.0 | — | 1.2 |
| NTA trisodium salt 40% strength aqueous solution | — | 15.0 | — | 15.0 |
| Noramer ® 2000[2)] | 0.4 | 0.4 | 0.4 | 0.4 |
| p-Hydroxybenzoic acid methyl ester | 0.5 | 0.5 | 0.5 | 0.5 |
| N-Acylglutamate | 0.4 | 0.4 | 0.4 | 0.4 |
| Water (demineralized) | 75.7 | 64.7 | 83.7 | 66.5 |
| pH of the concentrate | 8.5 | 9.6 | 10.1 | 9.4 |
| pH of a 1% strength aqueous solution (in demineralized water) | 8.0 | 9.8 | 9.8 | 9.9 |

[1)]Diester of phosphoric acid with butanol and ethylene glycol
[2)]Complexing agent based on carboxylate/sulphonate acrylic copolymers, from Norso Haas S.A., Verneuil, En Halatte, France Examples 1 and 3 in accordance with the table relate to concentrates which are free of complexing agents and behave very gently towards anodized aluminium surfaces. Examples 2 and 4 relate to NTA-containing concentrates which are preferred when cleanser solution is made up using hard water. Example 4 in addition comprises a phosphoric ester which according to the invention has an inhibitory action on anodized aluminium surfaces, so that a cleanser made up using this concentrate behaves in a similarly gentle manner towards anodized aluminium as a cleanser in accordance with Examples 1 and 3.

Process Examples for Mechanical Cleaning

1. In a one-tank dishwasher, the instruments to be cleaned are initially prerinsed with cold water. The dishwasher is then filled with cold water and the cleaning composition concentrate according to Example 1 is added at a concentration of 1.5%. The cleaning solution is heated to 40–45° C. and kept for 5 min at this temperature. Post-rinsing is then carried out with water. Finally, a thermal-disinfection is carried out using demineralized water at 93° C. Post-rinsing is carried out simultaneously using this water.

2. Cleaning by the so-called RKI(BGA) programme Cold water (if appropriate after a prerinse) is charged into a one-tank dishwasher and a cleaning composition concentrate according to Example 4 is added at a concentration of 0.3 to 1.0%. The cleaning solution is heated continuously to 93° C. in a period of about 10 minutes and kept at this temperature for about 10 minutes with circulation. After draining off the heated solution, there is an intermediate rinse with cold water and, in a final step, the final rinse in which the water is heated to 70° C. (solely for the purpose of the subsequent more rapid drying).

3. Cleaning using a discontinuous conveyor unit.

In a discontinuous conveyor unit, the instruments to be cleaned are run successively through different cleaning chambers. In this process example, a 3-chamber unit is used.

In the first chamber, a precleaning with cold water is firstly carried out for a period of 30 s, then cleaning with a 1% strength aqueous concentration of the cleaning composition concentrate in accordance with Example 1 is carried out for a period of 5 min at a temperature of 40° C. Subsequently to this, post-rinsing is carried out for 30 s with water.

In the second chamber, the instruments are treated in an ultrasonic bath at 35° C. for 5.5 min with a 2% strength aqueous solution of the cleaning composition concentrate according to Example 1.

In the third chamber, a 6-minute post-rinsing and simultaneous thermal disinfection using demineralized water at 93° C. are carried out.

What is claimed is:

1. A method for cleaning instruments, comprising cleaning an instrument with an enzyme-free composition comprising at least 10% by weight of at least one alkanolamine wherein said composition has a pH of 6 to 10 in aqueous solution.

2. The method of claim 1, wherein said instrument is selected from the group consisting of medical instruments and surgical instruments.

3. The method of claim 1, wherein said alkanolamine has the following structure:

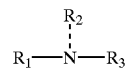

wherein $R_1$ is an hydroxyalkyl group having 1 to 6 carbon atoms, wherein $R_2$ is a hydroxyl group or hydrogen, and wherein $R_3$ is a hydroxyl group or hydrogen.

4. The method of claim 3, wherein said alkanolamine comprises at least one ethanolamine selected from the group consisting of monoethanolamine, diethanolamine, and triethanolamine.

5. The method of claim 1, wherein said composition has a pH of 7 to 9.

6. The method of claim 1, wherein said composition comprises at least one organic acid selected from the group consisting of monotricarboxylic acids, ditricarboxylic acids, and tricarboxylic acids, wherein said organic acid has two to six carbon atoms.

7. The method of claim 1, wherein said composition comprises at least one acid selected from the group consisting of citric acid, tartaric acid, malic acid, lactic acid, glycolic acid, glyoxylic acid, succinic acid, adipic acid, and glutaric acid.

8. The method of claim 1, wherein said composition comprises at least one complexing agent.

9. The method of claim 11, wherein said composition comprises at least one compound selected from the group consisting of nitriloacetic acid and salts of nitriloacetic acid.

10. The method of claim 9, wherein said composition further comprises at least one phosphoric acid selected from the group consisting of monodiester phosphoric acid and diester phosphoric acid, wherein said phosphoric acid further comprises alcohols selected from the group consisting of aliphatic alcohols with chain lengths of $C_1$ to $C_{22}$, aliphatic diols with chain lengths of $C_2$ to $C_{22}$, and aliphatic polyols with chain lengths of $C_2$ to $C_{22}$.

11. The method of claim 11, wherein said alkanolamine content of said composition is 10 to 40% by weight.

12. The method of claim 11, wherein said alkanolamine content of said composition is 10 to 20% by weight.

13. The method of claim 1, wherein said cleaning is mechanical.

14. A method for cleaning an apparatus, comprising cleaning an apparatus with an enzyme-free composition comprising at least 10% by weight of at least one alkanolamine wherein said composition has a pH of 6 to 10 in aqueous solution.

15. The method of claim 14, wherein said apparatus is selected from the group consisting of medical apparatus and surgical apparatus.

16. The method of claim 14, wherein said alkanolamine has the following structure:

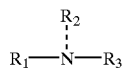

wherein $R_1$ is an hydroxyalkyl group having 1 to 6 carbon atoms, wherein $R_2$ is a hydroxyl group or hydrogen, and wherein $R_3$ is a hydroxyl group or hydrogen.

17. The method of claim 14, wherein said alkanolamine comprises at least one ethanolamine selected from the group consisting of monoethanolamine, diethanolamine, and triethanolamine.

18. The method of claim 14, wherein said composition has a pH of 7 to 9.

19. The method of claim 14, wherein said composition comprises at least one organic acid selected from the group consisting of monocarboxylic acids, dicarboxylic acids, and tricarboxylic acids, and wherein said organic acid has two to six carbon atoms.

20. The method of claim 14, wherein said composition comprises at least one acid selected from the group consisting of citric acid, tartaric acid, malic acid, lactic acid, glycolic acid, glyoxylic acid, succinic acid, adipic acid, and glutaric acid.

21. The method of claim 14, wherein said composition comprises at least one complexing agent.

22. The method of claim 21, wherein said composition comprises at least one compound selected from the group consisting of nitriloacetic acid and salts of nitriloacetic acid.

23. The method of claim 14, wherein said composition further comprises at least one phosphoric acid selected from the group consisting of monodiester phosphoric acid and diester phosphoric acid, wherein said phosphoric acid further comprises alcohols selected from the group consisting of aliphatic alcohols with chain lengths of $C_1$ to $C_{22}$, aliphatic diols with chain lengths of $C_2$ to $C_{22}$, and aliphatic polyols with chain lengths of $C_2$ to $C_{22}$.

24. The method of claim 14, wherein said alkanolamine content of said composition is 10 to 40% by weight.

25. The method of claim 24, wherein said alkanolamine content of said composition is 10 to 20% by weight.

26. The method of claim 14, wherein said cleaning is mechanical.

27. A method for cleaning instruments comprising the steps of:
   a) applying an aqueous solution of an enzyme-free cleaning composition concentrate to an instrument, wherein said solution comprises at least 10% by weight of at least one alkanolamine and has a pH of 6 to 10
   b) allowing the solution to act on said instrument; and
   c) rinsing said instrument.

28. The method of claim 27, wherein said cleaning composition concentrate is applied at a strength 0.5 to 20%.

29. The method of claim 27, wherein said acting in step b) is conducted at a temperature from room temperature to boiling temperature.

30. The method of claim 27, wherein said acting occurs for a time period of from two seconds to 10 minutes.

31. The method of claim 27 further comprising the step of thermal disinfection.

32. The method of claim 29, wherein said instrument is selected from the group consisting of medical instruments and surgical instruments.

33. A method for cleaning apparatus comprising the steps of:
   a) applying an aqueous solution of an enzyme-free cleaning composition concentrate to an apparatus, wherein said solution comprises at least 10% by weight of at least one alkanolamine and has a pH of 6 to 10
   b) allowing the solution to act on said apparatus; and
   c) rinsing said apparatus.

34. The method of claim 33, wherein said cleaning composition concentrate is applied at a strength of 0.5 to 20% strength.

35. The method of claim 33, wherein said acting in step b) is conducted at a temperature from room temperature to boiling temperature.

36. The method of claim 33, wherein said acting occurs for a time period of from two seconds to 10 minutes.

37. The method of claim 33, further comprising the step of thermal disinfection.

38. The method of claim 33, wherein said apparatus is selected from the group consisting of medical apparatus and surgical apparatus.

39. The method of claim 27, wherein said cleaning composition concentrate is applied at a strength of 0.5 to 10%.

40. The method of claim 27, wherein said cleaning composition concentrate is applied at a strength of 1 to 5%.

41. The method of claim 27, wherein said acting in step b) is conducted at a temperature from room temperature to 55° C.

42. The method of claim 27, wherein said acting in step b) is conducted at a temperature from 35 to 55° C.

43. The method of claim 27, wherein said acting in step b) is conducted at a temperature from 40 to 50° C.

44. The method of claim 27, wherein said acting occurs for a time period of from ten seconds to ten minutes.

45. The method of claim 27, wherein said acting occurs for a time period of from 30 seconds to five minutes.

46. The method of claim 33, wherein said cleaning composition concentrate is applied at a strength of 0.5 to 10%.

47. The method of claim 33, wherein said cleaning composition concentrate is applied at a strength of 1 to 5%.

48. The method of claim 33, wherein said acting in step b) is conducted at a temperature from room temperature to 55° C.

49. The method of claim 33, wherein said acting in step b) is conducted at a temperature from 35 to 55° C.

50. The method of claim 33, wherein said acting in step b) is conducted at a temperature from 40 to 50° C.

51. The method of claim 33, wherein said acting occurs for a time period of from ten seconds to ten minutes.

52. The method of claim 33, wherein said acting occurs for a time period of from 30 seconds to five minutes.

* * * * *